United States Patent [19]

Garabedian

[11] Patent Number: Plant 5,905

[45] Date of Patent: Mar. 17, 1987

[54] PLUM TREE, "BLACK JEWEL"

[76] Inventor: John M. Garabedian, 3104 E. Huntington Blvd., Fresno, Calif. 93702

[21] Appl. No.: 766,550

[22] Filed: Aug. 19, 1985

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Friar Plum Tree (unpatented), but which is distinguished therefrom by having a more pronounced red skin color, a smoother textured surface, and a unique, attractive light diffused red flesh which is aromatic and of excellent eating quality and which ripens approximately the second week of July.

1 Drawing Figure

BACKGROUND OF THE NEW VARIETY

The present invention relates to a new variety of plum tree, designated varietally as the "Black Jewel", and more particularly to a plum tree which bears fruit which ripens during the second week of July, approximately July 7 through July 14, and which is most closely similar to the "Friar" variety plum tree (unpatented), but which is distinguished therefrom by bearing clingstone plums, having a smoother skin surface, a more distinctive reddish skin color, and particularly by its unique, attractive and lightly red highlighted flesh which is aromatic and of excellent eating quality.

For many years, the applicant has engaged in the production of new and distinctive varieties of plum trees. The subject variety of plum tree was produced in one of the inventor's numerous new seedling areas but from parents of unknown origin. The subject variety plum tree was grown, with other seedlings, on the applicant's ranch near the intersection of Kings Canyon Road and Fowler Avenue in Fresno, County of Fresno, State of California, in 1977. When the unique qualities of the subject variety were recognized, the applicant asexually reproduced the new variety by budding the new variety to stock plum trees planted on his Ranch No. 9 located at the corner of Fowler Avenue and Belmont Avenue near the City of Fresno, Calif. The budded progeny were grown until it was determined that the new variety dependably and accurately reproduced the superior characteristics observed by the applicant in the original seedling. The applicant accomplished the aforementioned first propogation in 1980.

The instant variety is distinguishable from the "Friar" variety (unpatented), by its full Dark Maroon Red skin and somewhat diffused red flesh, which ripens during the second week of July, which further is aromatic and of excellent eating quality and which is a clingstone.

BRIEF DESCRIPTION OF THE DRAWING

The accompanying drawing is a color photograph of a characteristic twig bearing typical leaves, a cluster of two plums showing their external colorations sufficiently mature for harvesting and shipment, three mature plums of the color when matured on the trees, a plum halved transversely of the suture plane to illustrate the flesh coloration and five stones, all of the subject variety.

DETAILED DESCRIPTION

Referring more specifically to the pomological details of this new and distinct variety of plum tree, the following has been observed under the ecological conditions prevailing in the designated orchard in Fresno, County of Fresno, Calif. All major color code designations are by reference to the Munsell Limit Color Cascade. Common descriptive color names are also occasionally used.

TREE

Size: Medium to large, depending upon pruning practices.

Vigor: Medium.

Figure: Upright, spreading, dense and vase-formed, pruned to shape.

Productivity: Productive.

Regularity of bearing: Regular.

Trunk:

- *Thickness.*—Medium.
- *Texture of bark.*—Medium.

Branches:

- *Thickness.*—Medium.
- *Texture.*—Medium.
- *Color.*—Dark Gray Brown with narrow striations of lighter color.
- *Lenticels.*—Average in number, medium in size.

LEAVES

Shoot:

- *Size.*—Medium to large.
- *Length.*—11.03±1.29 cm.
- *Width.*—4.95±0.72 cm.
- *Form.*—Broadly oval, to broad obovate; acuminate; pointed to acutely pointed.
- *Thickness.*—Medium.
- *Color.*—Medium to Dark Green. Ventral Surface — (MCC 16-13), Dorsal Surface — somewhat lighter and grayer (MCC 22-12).
- *Texture.*—Nearly smooth.
- *Marginal form.*—Crenate.
- *Petiole.*—Medium in length; medium in thickness.
- *Glands.*—Variable, in a range of 2 to 4 in number; opposite and alternate in position; medium to large in size; mixed in shape; green; positioned at the base of the blade and apically on the petiole.

*Stipules.*—Linear.

Spur:

*Size.*—Small.

*Length.*—8.45±1.38 cm.

*Width.*—2.73±0.45 cm.

*Form.*—Narrow and slightly obovate, acuminate, pointed.

*Thickness.*—Medium.

*Color.*—Ventral surface, Dark Green (MCC 20-14 to 21-14); Dorsal surface, lighter and somewhat grayer color.

*Texture.*—Nearly smooth.

*Marginal form.*—Crenate.

*Petiole.*—Length — medium, Thickness — medium to slender.

*Glands.*—Variable in number, averaging one to two; usually opposite in position, very small in size; variable in shape; green in color; positioned at the base of the blade.

*Stipules.*—Completely lacking in the spur.

Flower buds: Small, conic, plump, free and glabrous.

Flowers: Medium in size, white in color.

*Date of first bloom.*—Feb. 28, 1984.

*Date of full bloom.*—Mar. 2, 1984; average date of bloom as compared with other varieties.

FRUIT

Maturity when described: Full ripeness, August 8.

Size: Somewhat variable, medium to large.

*Axial diameter.*—6.04±0.18 cm.

*Diameter transverse in suture plane.*—5.99±0.22 cm.

*Diameter transverse in cheek plane.*—6.32±0.19 cm.

Suture: An inconspicuous, very shallow and broad groove extending from the base to the apex.

Ventral surface: Rounded, and very slightly lipped throughout; one lip is generally larger and broader.

Cavity: Rounded and occasionally abrupt, circular; elongated in the suture plane with the suture showing on one side.

*Depth of the cavity.*—1.36±0.13 cm.

*Breadth of the cavity.*—2.30±0.09 cm.

*Markings.*—None.

Base: Rounded or occasionally truncated.

Apex: Occasionally prolonged; rounded.

Pistil point: Oblique.

Skin: Thin to medium in thickness; tender to medium in texture; tenacious to flesh; no observed tendency to crack.

*Color.*—Dark Maroon Red (MCC 39-16).

*Dots.*—Few, often only located at the apex, small, Light Brown, otherwise scattered throughout.

*Bloom.*—Moderately heavy; Blue-Gray in color, (MCC 3-5).

Stem: Medium in length, approximately 2 cm.; moderately stout as compared with other varieties.

Flesh:

*Color.*—Pale, very light Amber near the stone (MCC 29-2); a light, diffused Red (MCC 39-6) near the skin surface; the light Red is diffused and not streaked; the color on the surface of the pit cavity is somewhat darker than the flesh adjacent to the pit cavity.

*Amygdalin.*—Wanting.

*Juice.*—Moderate in amount, rich in quality.

*Texture.*—Soft and fine; melting to meaty in texture.

*Fibers.*—Few and fine.

*Ripening.*—Even.

*Flavor.*—Mild and vinous.

*Aroma.*—Distinct.

*Eating quality.*—Good to excellent.

Stone: Cling.

*Size.*—Medium.

*Length.*—2.31±0.14 cm.

*Breadth.*—1.45±0.07 cm.

*Thickness.*—0.97±0.03 cm.

*Form.*—In the cheek view, a narrow oval.

*Base.*—Dorsally oblique.

*Hilum.*—Broad and oblong.

*Apex.*—Acuminate.

*Sides.*—Unequal, ventral longer.

*Surface.*—Nearly smooth medianly; lightly rugose apically; lightly ridged and furrowed basally; ridges more or less sharp and jagged.

*Ventral edge.*—Thick with wing throughout, but often eroded.

*Dorsal edge.*—Narrow with a shallow groove located toward the base to above center.

*Ridges.*—Located on either side, continuous but very low.

*Color of stone.*—Light Tan (MCC 29-1).

*Tendency to split.*—Slight.

Use: Market, local and dessert.

Keeping Quality: Medium.

Resistance to insects: Not observed.

Resistance to diseases: Not observed.

Shipping quality: Medium to good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control shall be expected.

Having thus described and illustrated my new variety of plum tree, I claim:

1. A new and distinct variety of plum tree substantially as illustrated and described which is somewhat similar to the Friar variety (unpatented), but from which it is distinguished by bearing clingstone fruit that has a more pronounced red surface color, a smoother textured surface, and by its unique attractive red flesh which is aromatic and of excellent eating quality.

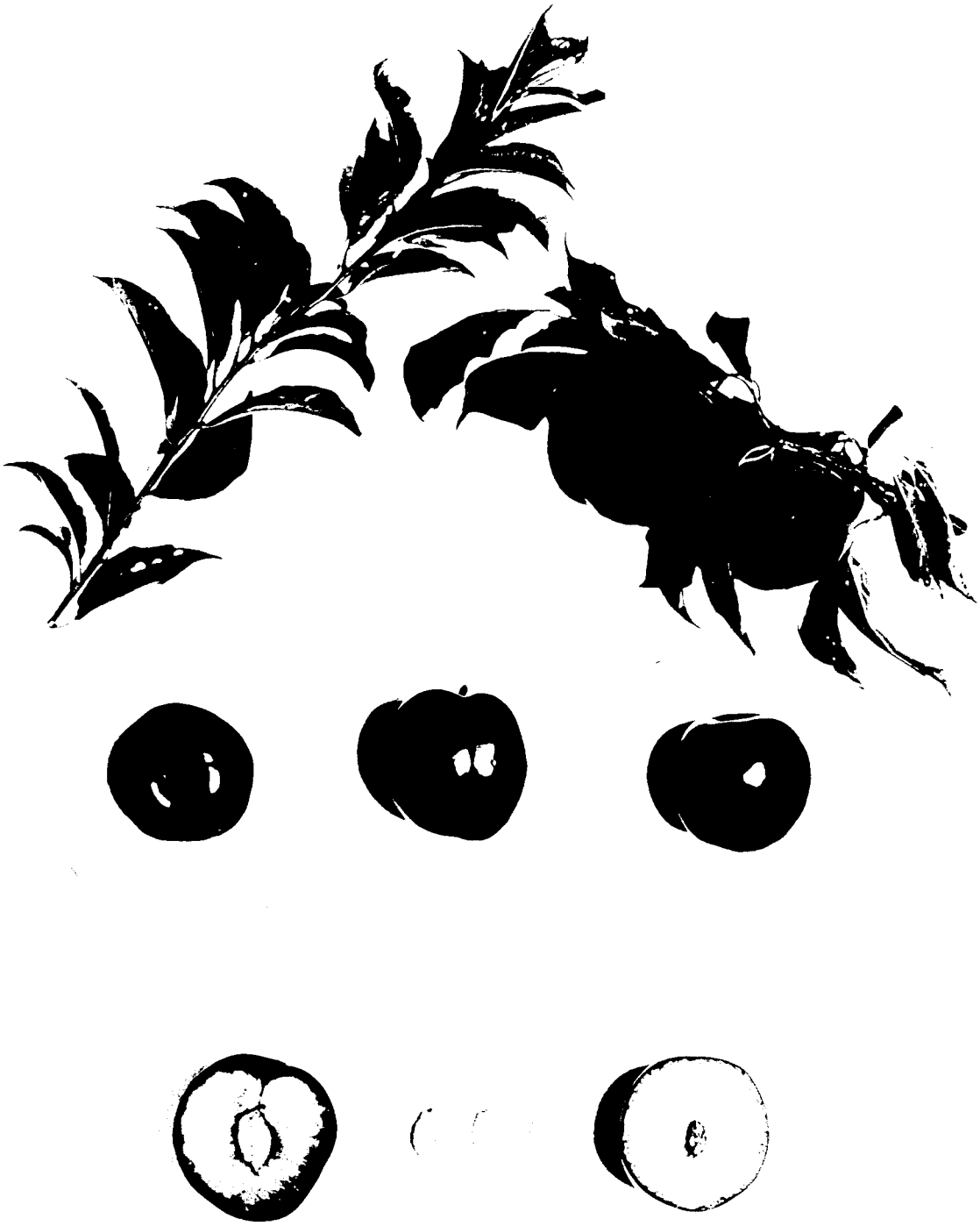

* * * * *